United States Patent
Wainscott

(10) Patent No.: US 10,226,289 B2
(45) Date of Patent: Mar. 12, 2019

(54) ANATOMIC DISTAL FIBULA PLATE WITH ANTEROLATERAL DIRECTED SYNDESMOSIS SCREW HOLES

(71) Applicant: Biomet Manufacturing, LLC, Warsaw, IN (US)

(72) Inventor: Chad Wainscott, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 307 days.

(21) Appl. No.: 14/991,266

(22) Filed: Jan. 8, 2016

(65) Prior Publication Data

US 2016/0262814 A1 Sep. 15, 2016

Related U.S. Application Data

(60) Provisional application No. 62/101,734, filed on Jan. 9, 2015.

(51) Int. Cl.
*A61B 17/80* (2006.01)
*A61B 17/68* (2006.01)

(52) U.S. Cl.
CPC .... *A61B 17/8061* (2013.01); *A61B 2017/681* (2013.01)

(58) Field of Classification Search
CPC .......................... A61B 17/80; A61B 17/8061
See application file for complete search history.

(56) References Cited

U.S. PATENT DOCUMENTS

| | | | |
|---|---|---|---|
| 7,235,091 B2 | 6/2007 | Thornes | |
| 2007/0239163 A1* | 10/2007 | Strnad | A61B 17/8047 606/286 |
| 2012/0172936 A1* | 7/2012 | Horrell | A61B 17/0401 606/319 |
| 2014/0107798 A1* | 4/2014 | Jeng | A61F 2/4202 623/21.18 |

* cited by examiner

*Primary Examiner* — Christopher Beccia
(74) *Attorney, Agent, or Firm* — Schwegman Lundberg & Woessner, P.A.

(57) ABSTRACT

An apparatus can include a fibula plate having a shape such that, when placed on a fibula, includes a distal portion facing in a lateral direction and an upper portion wrapped around to a posterior aspect of the fibula, the fibula plate having screw holes positioned in the upper portion to direct screws anteromedially rather than directly medial.

22 Claims, 4 Drawing Sheets

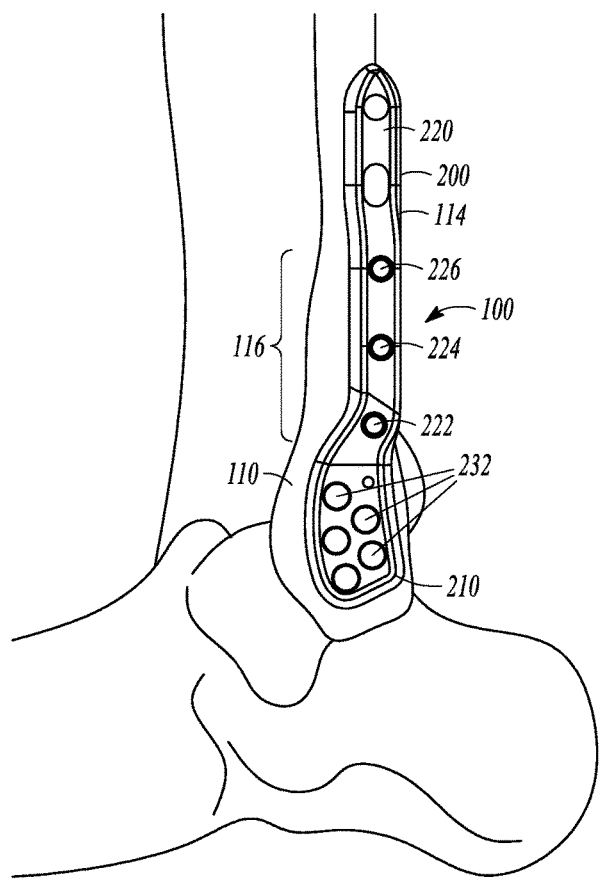
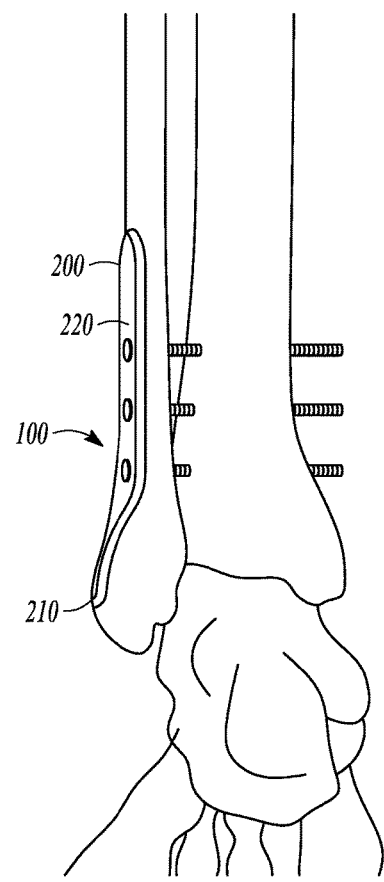
FIG. 2
FIG. 3

US 10,226,289 B2

ANATOMIC DISTAL FIBULA PLATE WITH ANTEROLATERAL DIRECTED SYNDESMOSIS SCREW HOLES

CLAIM OF PRIORITY

This application claims the benefit of U.S. Provisional Patent Application Ser. No. 62/101,734, filed on Jan. 9, 2015, the benefit of priority of which is claimed hereby, and is incorporated by reference herein in its entirety.

FIELD

The present subject matter relates to an orthopedic system and specifically to a distal fibula plate.

BACKGROUND

An ankle injury that includes syndesmosis ligament disruption is often accompanied by distal fibula comminution and/or a Weber C fibular fracture. In such a case, the syndesmosis ligaments that connect the fibula to the tibia are torn or ruptured and as a result, the relative motion of the fibula to the tibia must be constrained by surgical hardware to allow the ligaments to heal.

The standard of care for an ankle syndesmosis injury is to rigidly affix the fibula to the tibia using one or more screws that pass through the fibula and into the tibia. The screws should be in a transverse plane and angled to pass through the center of the fibula and the tibia incisura. When an anatomic lateral distal fibula plate is necessary to correct the fibular fracture, it is desirable to place syndesmosis screws through the plate to correct a more rigid construct.

Current anatomic distal fibula plates are designed to sit on the lateral aspect of the fibula. Screw holes in the syndesmotic repair region are perpendicular to the surface of such a plate, thus screwing through the plate at the proper angle to correctly reduce the fibula (roughly 30° anterior) is constrained by the off axis screw angle limitations of the hole. Additionally, even if it is angled properly, if the plate sits directly lateral then the origin of the hole is often too far anterior to pass through the midline of the fibula and tibial incisura. U.S. Pat. No. 7,235,091 discusses a method for fixation of ankle syndesmosis.

OVERVIEW

In Example 1, a fibula plate can have a shape such that, when placed on a fibula, includes a distal portion facing in a lateral direction and an upper portion wrapped around to a posterior aspect of the fibula. The fibula plate can have screw holes positioned in the upper portion to direct screws anteromedially rather than directly medial.

In Example 2, the fibula plate of Example 1 optionally can wrap around the posterior aspect of the fibula in a syndesmotic screw region.

In Example 3, the fibula plate of Example 1 can optionally wrap around the posterior aspect of the fibula such that the screw holes are positioned approximately perpendicular to a 30° anterior plane.

In Example 4, the fibula plate of Example 1 can optionally include the distal portion the fibula plate sitting directly lateral on the fibula.

In Example 5, the fibula plate of Example 1 can optionally include the upper portion of the fibula plate directing screws through the middle of the fibula and the tibial incisura.

In Example 6, the fibula plate of Example 1 can optionally include screw holes in the distal portion of the fibula plate.

In Example 7, the fibula plate of Example 6 can optionally include the screw holes permitting one or more screws to be placed for distal fibula comminution repair.

In Example 8, the fibula plate can optionally include the screw holes in the upper portion directing screws approximately 30° anterior to the coronal plane.

These examples can be combined in any permutation or combination. This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 2 shows a side view of a fibula plate on an ankle, in accordance with one embodiment.

FIG. 3 shows back view of the fibula plate of FIG. 2.

DETAILED DESCRIPTION

Figure 1:
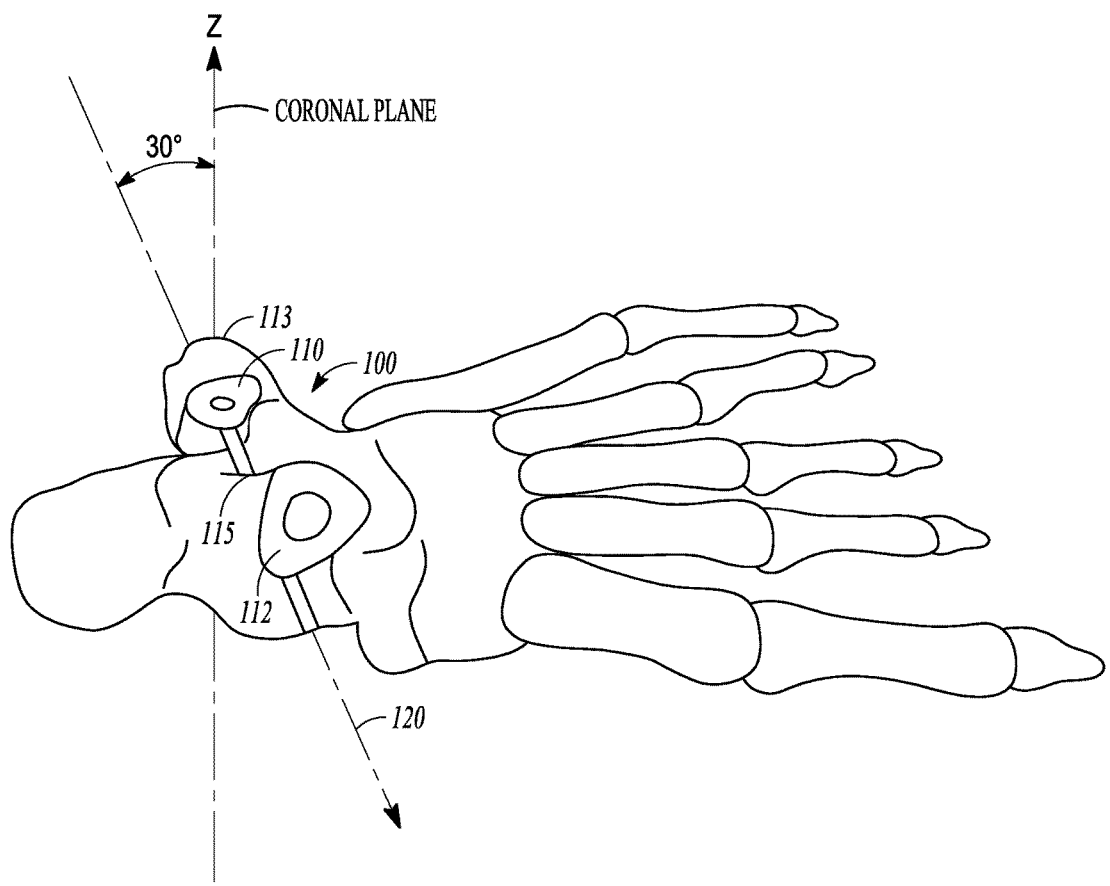
FIG. 1 shows a top view of an ankle.
Figure 4:
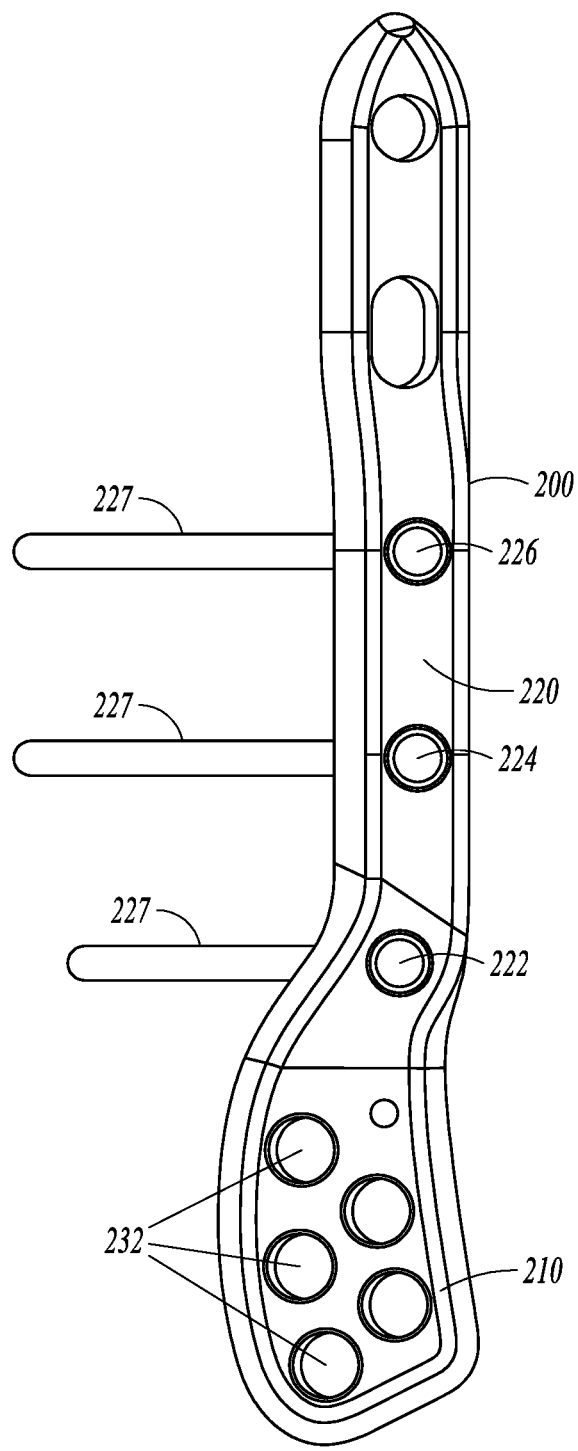
FIG. 4 shows a perspective view of a fibula plate, in accordance with one embodiment.

FIG. 1 shows a top view of an ankle 100 with the fibula 110 and the tibia 112. The Z-vector represents the lateral direction in the coronal plane. Sign 113 points to the direct lateral face of the distal fibula 110. Guideline 120 represents a desired direction for screws to go through the fibula 110 and the syndesmosis region of the ankle. As is shown, the desired trajectory for the screws is about 30° anterior to the coronal plane (or, perpendicular to the 30° anterior plane).

Figure 5:
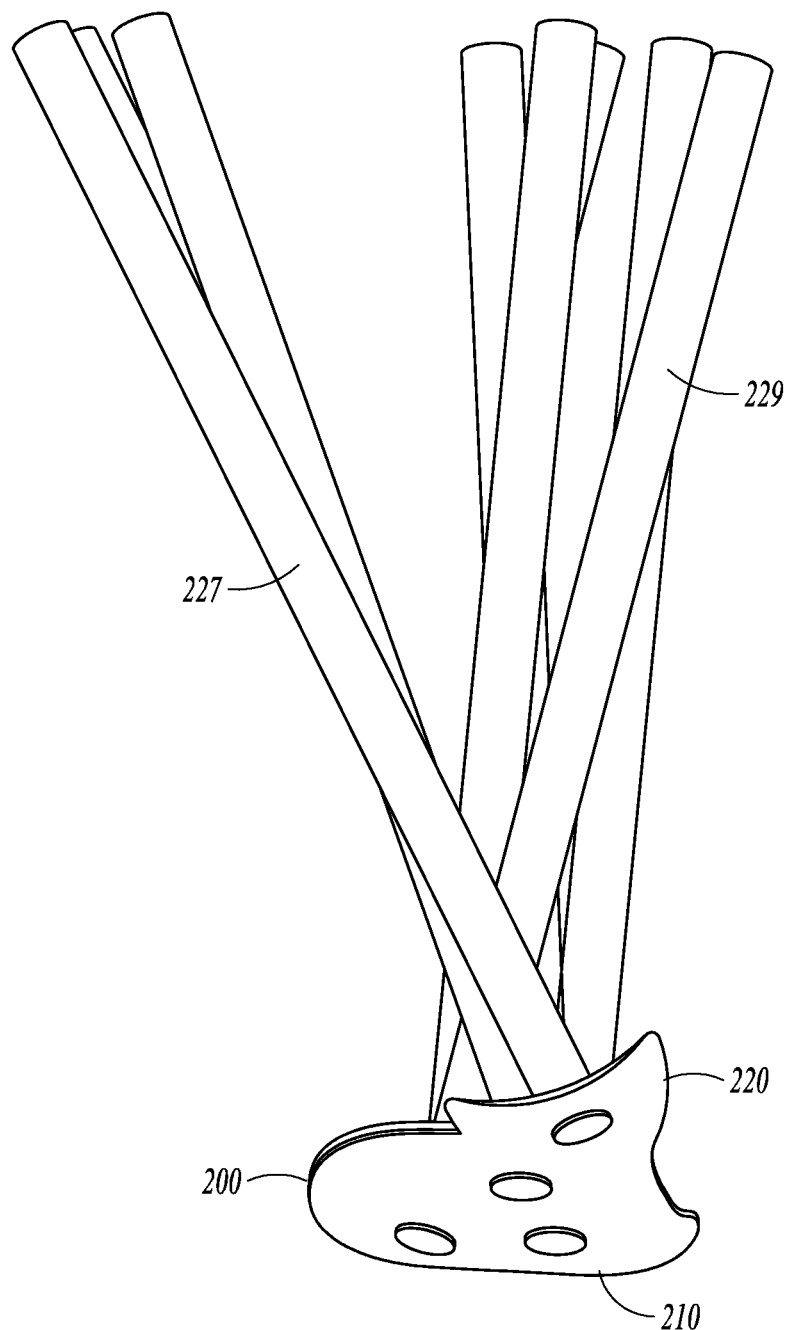
FIG. 5 shows a top view of a fibula plate, in accordance with one embodiment.

FIGS. 2, 3, 4d 5 show a fibula plate 200, in accordance with one embodiment. FIG. 2 shows a side view of the fibula plate 200 on the ankle 100. FIG. 3 shows back view of the fibula plate 200, FIG. 4 shows a perspective view of the fibula plate 200, and FIG. 5 shows a top view of a fibula plate 200.

In this example, the fibula plate 200 can include a shape including a distal portion 210 facing in a lateral direction, when placed on the fibula 110, and an upper portion 220 which can be wrapped around to a posterior aspect 114 of the fibula 110. The fibula plate 200 can include one or more screw holes 222, 224, 226 positioned in the upper portion 220 to direct one or more screws 227 anteromedially rather than directly medial.

Accordingly, the distal portion 210 of the fibula plate 200 is positioned on the direct lateral face of the fibula 110 to repair and protect any distal comminution of the fibula 110, while the upper portion 220 wraps around to the posterior aspect 114 of the fibula 110 and positioned to place syndesmosis screws at an angle that will not tend to malreduce the fibula.

It is noted that any screw that does not pass through the center line 115 (FIG. 1) of the tibial incisura can tend to malreduce the fibula. The tibial incisura, also called the fibular notch of the tibia, is an indentation at the inferior portion of the tibia where it articulates with the fibula. As noted in FIG. 1, the desired angle through the fibula to pass through the center line 115 of the tibial incisura is about 30° anterior to the coronal plane. With current hardware, screws are often placed independent of a fibula plate, but many surgeons would prefer to pass the screws through the plate to improve the strength and rigidity of the construct. Thus, in general, fibula plate 200 allows for desired comminution of a fibula injury while also allowing for desired placement of the screws 227 to heal a syndesmosis ligament injury.

Here, the fibula plate 200 wraps around the posterior aspect 114 of the fibula 100 in a syndesmotic screw region 116. In one example, the fibula plate 200 wraps around the posterior aspect 114 of the fibula 100 such that the screw holes 222, 224, and 226 are positioned approximately perpendicular to the 30° anterior plane. In one example, the distal portion 210 of the fibula plate 200 can sit directly lateral on the fibula 100. The upper portion 220 of the fibula plate 200 wraps around to the posterior aspect of the fibula 100, approximately perpendicular to the 30° anterior plane and can direct the screws 227 through the middle of the fibula and the tibial incisura. Thus, the screw holes 222, 224, 226 in the upper portion 220 can direct screws approximately 30° anterior to the coronal plane.

In one example, the fibula plate can include one or more screw holes 232 in the distal portion 210 of the fibula plate 200. Screw holes 232 can permit one or more screws 229 or sutures to be placed for distal fibula comminution repair.

The fibula plate 200 can be formed of a surgical metal or ceramic and can be molded, bent, or otherwise shaped to have the proper anatomical curvature as described herein.

In use, the surgeon places the fibula plate 200 such that the distal portion 210 sits directly lateral on the fibula 100 while the upper portion 220 curves or wraps around to the posterior aspect 114 of the fibula 100 such that the upper portion 220 lies approximately perpendicular to the 30° anterior plane. On or more screws 22 can be placed though holes 222, 224, 226, or 232 to allow for syndesmosis repair and for distal comminution repair of the fibula 200.

As shown in FIG. 5, the geometry and shape of the fibula plate 200 results in an approximately 30° angle between screws 227 and screws 229. Fibula plate 200 can be formed in differing sizes relative to the size of the patient, while still having the same generally shape and anatomical geometry as described herein.

ADDITIONAL NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The claimed invention is:

1. An apparatus comprising:
  a fibula plate having a shape such that, when placed on a fibula, includes a distal portion facing in a lateral direction and an upper portion and a central portion located between the distal portion and the upper portion, wherein the central portion includes a twist around a longitudinal axis of the fibula plate such that the upper portion is wrapped around to a posterior aspect of the fibula;
  the fibula plate having screw holes positioned in the upper portion to direct screws anteromedially rather than directly medial, wherein the holes are structured and oriented to guide screws first through the fibula and then into the tibia; and
  at least two screws that are insertable through the screw holes such that the at least two screws are inserted first through the fibula and then through the tibia when implanted.

2. The apparatus of claim 1, wherein the fibula plate wraps around the posterior aspect of the fibula in a syndesmotic screw region.

3. The apparatus of claim 1, wherein the fibula plate wraps around the posterior aspect of the fibula such that the screw holes are positioned approximately perpendicular to a 30° anterior plane.

4. The apparatus of claim 1, wherein the distal portion the fibula plate sits directly lateral on the fibula.

5. The apparatus of claim 1, wherein the upper portion of the fibula plate directs screws through the middle of the fibula and the tibial incisura.

6. The apparatus of claim 1, further including screw holes in the distal portion of the fibula plate.

7. The apparatus of claim 6, wherein the screw holes permit one or more screws to be placed for distal fibula comminution repair.

8. The apparatus of claim 1, wherein the screw holes in the upper portion direct screws approximately 30° anterior to the coronal plane.

9. An apparatus comprising:
  a fibula plate shaped such that, when place on a fibula, the fibula plate includes a distal portion facing a lateral section of a distal fibula and an upper portion which curves relative to the distal portion so as to face a posterior aspect of the fibula in a syndesmotic screw region and allow syndesmotic screws to be directed in an anteromedial direction rather than a medial direction, wherein the fibula plate includes a central portion located between the distal portion and the upper portion, wherein the central portion includes a twist around a longitudinal axis of the fibula plate such that the entire surface of the upper portion is angled relative to the distal portion; and at least two screws that are insertable through the screw holes such that the at least two screws are inserted first through the fibula and then through the tibia when implanted.

10. The apparatus of claim 9, wherein the fibula plate includes screw holes in the portion of the plate located in the syndesmotic screw region.

11. The apparatus of claim 10, wherein the fibula plate wraps around the posterior aspect of the fibula such that the screw holes are positioned approximately perpendicular to a 30° anterior plane.

12. The apparatus of claim 10, wherein the screw holes direct syndesmotic screws approximately 30° anterior to the coronal plane.

13. The apparatus of claim 9, wherein the distal portion the fibula plate sits directly lateral on the distal fibula.

14. The apparatus of claim 9, wherein the portion of the fibula plate located in the syndesmotic screw region directs screws through the middle of the fibula and the tibial incisura.

15. The apparatus of claim 9, further including screw holes in the distal portion of the fibula plate.

16. The apparatus of claim 15, wherein the screw holes permit one or more screws to be placed for distal fibula comminution repair.

17. A method comprising:
placing a fibula plate so that a distal portion of the fibula plate faces in a lateral direction on a fibula an upper portion of the fibula plate wraps around to a posterior aspect of the fibula, and wherein the fibula plate includes a central portion located between the distal portion and the upper portion, wherein the central portion includes a twist around a longitudinal axis of the fibula plate such that the entire surface of the upper portion is angled relative to the distal portion; and
placing two or more screws through the upper portion of the fibula plate in an anteromedially direction such that the two or more screws pass though the fibula and into a tibia.

18. The method of claim 17, wherein the screw are placed in the syndesmotic region.

19. The method of claim 17, wherein the screws are directed in a direction approximately 30° anterior to the coronal plane.

20. The method of claim 17, wherein the screws are directed through the middle of the fibula and the tibial incisura.

21. The apparatus of claim 1, wherein all of the screw holes in the upper portion direct screws anteromedially rather than directly medial.

22. The apparatus of claim 1, wherein at least three screws are insertable through the screw holes such that the at least three screws are inserted fort though the fibula and then through the tibia when implanted.

* * * * *